US012201456B2

(12) United States Patent
Folk et al.

(10) Patent No.: US 12,201,456 B2
(45) Date of Patent: Jan. 21, 2025

(54) SYSTEMS FOR DIAGNOSING AND/OR TREATING MEDICAL CONDITIONS (71) Applicant: Covidien LP, Mansfield, MA (US)

(72) Inventors: Christopher Folk, Los Angeles, CA (US); Jacob Kearns, Laguna Hills, CA (US)

(73) Assignee: Covidien LP, Mansfield, MA (US)

( * ) Notice: Subject to any disclaimer, the term of this patent is extended or adjusted under 35 U.S.C. 154(b) by 1055 days.

(21) Appl. No.: 16/864,537

(22) Filed: May 1, 2020

(65) Prior Publication Data

US 2020/0253563 A1 Aug. 13, 2020

Related U.S. Application Data (62) Division of application No. 14/758,754, filed as application No. PCT/US2013/073810 on Dec. 9, 2013, now Pat. No. 10,674,966.

(Continued)

(51) Int. Cl.
*A61B 5/00* (2006.01)
*A61B 5/02* (2006.01)
(Continued)

(52) U.S. Cl.
CPC ........ *A61B 5/7278* (2013.01); *A61B 5/02014* (2013.01); *A61B 5/0215* (2013.01);
(Continued)

(58) Field of Classification Search
CPC ... A61B 5/0215; A61B 5/026; A61B 5/02007; A61B 6/504; A61B 17/12031; A61B 17/12036; A61B 17/1204; A61B 17/1214; A61B 2017/00022; A61B 2017/00026; A61B 2017/00039; A61B 2017/22081; A61B 2017/22094; A61M 2025/0002
See application file for complete search history.

(56) References Cited

U.S. PATENT DOCUMENTS 5,580,568 A 12/1996 Greff et al.
5,667,767 A 9/1997 Greff et al.
(Continued)

FOREIGN PATENT DOCUMENTS

WO 2008139347 A1 11/2008

OTHER PUBLICATIONS

International Preliminary Report on Patentability from International Application No. PCT/US2013/073810, mailed Jun. 25, 2015, 8 pp.
(Continued)

*Primary Examiner* — Devin B Henson
(74) *Attorney, Agent, or Firm* — Shumaker & Sieffert, P.A.

(57) ABSTRACT

A method for performing a diagnostic or therapeutic procedure on a partial occlusion within a blood vessel, includes positioning a guide having a sensor configured and adapted to measure at least one of pressure, volume or flow within a blood vessel, advancing the guide through an at least partial occlusion within the blood vessel such that the sensor is downstream of the occlusion, measuring at least one of pressure, volume or flow downstream of the occlusion using the sensor and analyzing data obtained from the sensor to assist in determining the viability of tissue of the blood vessel downstream of the occlusion.

10 Claims, 7 Drawing Sheets

Related U.S. Application Data (60) Provisional application No. 61/735,694, filed on Dec. 11, 2012.

(51) Int. Cl.

| | | |
|---|---|---|
| *A61B 5/0215* | (2006.01) | |
| *A61B 5/026* | (2006.01) | |
| *A61B 5/027* | (2006.01) | |
| *A61B 6/03* | (2006.01) | |
| *A61B 6/50* | (2024.01) | |
| *A61B 17/12* | (2006.01) | |
| *A61F 2/90* | (2013.01) | |
| *A61B 17/00* | (2006.01) | |
| *A61B 17/22* | (2006.01) | |
| *A61B 17/3207* | (2006.01) | |
| *A61B 90/00* | (2016.01) | |
| *A61F 2/82* | (2013.01) | |

(52) U.S. Cl.
CPC .............. *A61B 5/026* (2013.01); *A61B 5/027* (2013.01); *A61B 5/4848* (2013.01); *A61B 5/6851* (2013.01); *A61B 5/6852* (2013.01); *A61B 5/7246* (2013.01); *A61B 6/032* (2013.01); *A61B 6/504* (2013.01); *A61B 17/12118* (2013.01); *A61B 17/1214* (2013.01); *A61F 2/90* (2013.01); *A61B 2017/00022* (2013.01); *A61B 2017/22082* (2013.01); *A61B 17/3207* (2013.01); *A61B 2090/063* (2016.02); *A61B 2090/064* (2016.02); *A61F 2002/823* (2013.01)

(56) References Cited

U.S. PATENT DOCUMENTS

| | | | |
|---|---|---|---|
| 5,695,480 | A | 12/1997 | Evans et al. |
| 5,715,827 | A | 2/1998 | Corl et al. |
| 5,851,508 | A | 12/1998 | Greff et al. |
| 6,167,763 | B1 | 1/2001 | Tenerz et al. |
| 6,295,990 | B1 * | 10/2001 | Lewis .................... A61B 17/22 604/509 |
| 6,767,327 | B1 | 7/2004 | Corl et al. |
| 6,976,965 | B2 | 1/2005 | Corl et al. |
| 6,986,744 | B1 | 1/2006 | Krivitski |
| 7,097,620 | B2 | 8/2006 | Corl et al. |
| 7,507,394 | B2 | 3/2009 | Whalen et al. |
| 7,524,303 | B1 | 4/2009 | Don Michael et al. |
| 7,666,220 | B2 | 2/2010 | Evans et al. |
| 7,699,059 | B2 | 4/2010 | Fonseca et al. |
| 7,918,800 | B1 | 4/2011 | Brown et al. |
| 8,088,140 | B2 | 1/2012 | Ferrera et al. |
| 8,257,421 | B2 | 9/2012 | Berez et al. |
| 8,267,986 | B2 | 9/2012 | Berez et al. |
| 9,314,584 | B1 * | 4/2016 | Riley .................... A61B 5/021 |
| 11,064,964 | B2 * | 7/2021 | Tolkowsky ............ A61B 5/021 |
| 2002/0183629 | A1 | 12/2002 | Fitz |
| 2003/0199772 | A1 | 10/2003 | Letort et al. |
| 2003/0229388 | A1 | 12/2003 | Hayashi et al. |
| 2004/0059407 | A1 | 3/2004 | Escamilla et al. |
| 2004/0167385 | A1 | 8/2004 | Rioux et al. |
| 2006/0106321 | A1 * | 5/2006 | Lewinsky ................ A61B 6/12 600/491 |
| 2006/0122691 | A1 | 6/2006 | Richter |
| 2009/0003521 | A1 * | 1/2009 | Camus .................... A61B 6/507 378/62 |
| 2010/0198329 | A1 | 8/2010 | Kassab et al. |
| 2010/0204634 | A1 | 8/2010 | Baxter et al. |
| 2010/0234698 | A1 * | 9/2010 | Manstrom ............. A61M 25/09 600/478 |
| 2011/0224606 | A1 | 9/2011 | Shome et al. |
| 2012/0187604 | A1 | 7/2012 | Karino et al. |
| 2016/0022222 | A1 | 1/2016 | Folk et al. |

OTHER PUBLICATIONS

International Search Report and Written Opinion from PCT Application No. PCT/US2013/073810, dated Feb. 27, 2014, 21 pgs.
"Blood pressure in the artery distal to an intraarterial embolus during thrombolytic therapy for occlusion of a major artery: a predictor of cerebral infarction following good recanalization" by Sorimachi et al., in the Journal of Neurosurgery 102:870-878 (May 2005).
Prosecution History from U.S. Appl. No. 14/758,754, dated Aug. 26, 2016 through May 7, 2020, 247 pp.

\* cited by examiner

SYSTEMS FOR DIAGNOSING AND/OR TREATING MEDICAL CONDITIONS

This application is a divisional of U.S. patent application Ser. No. 14/758,754, filed on Jun. 30, 2015, and entitled, "SYSTEMS FOR DIAGNOSING AND/OR TREATING MEDICAL CONDITIONS," which is a U.S. National Stage filing under 35 U.S.C. § 371 of International Application No. PCT/US2013/073810, filed Dec. 9, 2013, and entitled, "SYSTEMS FOR DIAGNOSING AND/OR TREATING MEDICAL CONDITIONS," which claims the benefit of U.S. Provisional Application No. 61/735,694, filed Dec. 11, 2012 and entitled, "SYSTEMS FOR DIAGNOSING AND/OR TREATING MEDICAL CONDITIONS." The entire content of U.S. patent application Ser. No. 14/758,754, International Application No. PCT/US2013/073810, and U.S. Provisional Application No. 61/735,694 is incorporated herein by reference in its entirety.

BACKGROUND

1. Technical Field

The present disclosure generally relates to medical systems and methods, and, in particular, relates to systems and associated methods for diagnosing and/or treating neurovascular conditions with the use of an intravascular guidewires or catheters having pressure, volume and/or flow sensing capabilities.

2. Description of Related Art

Typically, when a patient exhibits ischemic stroke conditions, magnetic resonance imaging (MRI), CT-perfusions, or both are generally used to determine whether the patient is a good candidate for a thrombectomy. However, such diagnostic procedures often take a substantial amount of time and can be quite expensive. When a patient has an aneurysm, the aneurysm may be filled with coils or may be bypassed via a stent. To determine whether an aneurysm is sufficiently coiled, the packing density of the coil may be measured. However, due to various conditions including aneurysm size, skill of the clinician, etc., measurement of the packing density may be inaccurate. To determine whether an aneurysm is sufficiently bypassed by a stent or filled via coiling, an angiogram is commonly used. However, an angiogram measures neither pressure, pressure drop, flow direction nor flow rate, and thus may not be the best indicator of effectiveness of the procedure.

SUMMARY

Accordingly, the present disclosure is directed to a method for performing a diagnostic or therapeutic procedure on a partial occlusion within a blood vessel, including:
positioning a guide having a sensor configured and adapted to measure at least one of pressure, volume or flow within a blood vessel;
advancing the guide through an at least partial occlusion within the blood vessel such that the sensor is downstream of the occlusion;
measuring at least one of pressure, volume or flow downstream of the occlusion using the sensor, and
analyzing data obtained from the sensor to assist in determining the viability of tissue of the blood vessel downstream of the occlusion.

In embodiments, the method further includes determining a surgical protocol based on analyzing the data. In some embodiments, the method further includes obtaining a CT scan of the blood vessel and/or the occlusion and wherein determining the surgical protocol includes reviewing the CT scan.

In certain embodiments, the method includes treating the occlusion. Treating the occlusion may include at least one of introducing a thrombectomy device to remove the occlusion, initiating drug therapy to treat the occlusion or implanting a stent or flow diverter adjacent the occlusion. In embodiments, measuring at least one of pressure, volume or flow downstream of the occlusion using the sensor is also performed subsequent to treating the occlusion to test effectiveness thereof.

The method also may include measuring at least one of pressure, volume or flow upstream of the occlusion using the sensor. In embodiments, analyzing data includes comparing measurements obtained by the sensor upstream and downstream of the occlusion.

In another aspect, a method for performing a diagnostic or therapeutic procedure on an aneurysm, includes:
introducing an intravascular device through a parent vessel and adjacent an aneurysm to reduce blood flow from the parent vessel into the aneurysm;
advancing a guide through the parent vessel;
positioning a sensor of the guide at least adjacent to the aneurysm; and
measuring at least one of pressure, volume or blood flow velocity adjacent the aneurysm with the sensor to determine the effectiveness of the intravascular device in minimizing blood flow from the parent vessel into the aneurysm.

In embodiments, the method includes obtaining a CT scan to assist in determining the effectiveness of the intravascular device.

In some embodiments, positioning the sensor includes disposing the sensor within the aneurysm. In other embodiments, positioning the sensor includes disposing the sensor upstream of the aneurysm and measuring at least one of pressure, volume or blood flow velocity with the sensor, and disposing the sensor downstream of the aneurysm and measuring at least one of pressure, volume or blood flow velocity with the sensor, and further including comparing data obtained via these measurements.

In embodiments, introducing the intravascular device includes delivering a plurality of microcoils within the aneurysm to at least partially occlude the aneurysm, delivering an embolic material into the aneurysm, and/or positioning a stent to traverse the aneurysm and thereby divert blood flow away from the aneurysm.

In embodiments, the method further includes delivering an auxiliary intra-aneurysm device adjacent the stent and into the aneurysm based on detected changes in pressure, volume or blood flow velocity. Delivering an auxiliary intra-aneurysm device may include delivering an embolic material and/or microcoils into the aneurysm.

In some embodiments, introducing the intravascular device includes advancing the intravascular device through a lumen of the guide.

BRIEF DESCRIPTION OF THE DRAWINGS

Embodiments of the present disclosure will be readily appreciated by reference to the drawings wherein.

DESCRIPTION

In the following description, the terms "proximal" and "distal" as used herein refer to the relative position of the system in a body lumen such as a blood vessel, e.g., in the neurovascular region. The "proximal" or "trailing" end of the system, which includes a guide (e.g., guidewire or catheter), is the portion that is closest to the clinician. The "distal" or "leading" end of the system or guide is the portion that is placed farthest into a body lumen from the entrance site.

The methods and systems of the present disclosure have particular application in neurovascular procedures, but may be used in any interventional, diagnostic, and/or therapeutic procedure including coronary vascular, peripheral vascular, and gastro-intestinal applications in addition to a neurovascular application.

As used herein, the term "guide" is used to mean guidewires, catheters (e.g., catheters that slide over guidewires) and/or microcatheters. In the figures below, the full length of the guide of the disclosed system is not shown. If a guidewire is used, the length of a guidewire can vary depending on the type of interventional procedure or method, though typically it ranges in length from 30 centimeters to 400 centimeters (cm). Common lengths of guidewires for coronary, peripheral and neurovascular procedures may range from 150 (or less) cm to 300 cm in length. These lengths permit the use of standardized rapid exchange or over-the-wire catheter systems. The length of the shaped distal end also may vary, for example, from about 3 cm to about 80 cm in length.

The various embodiments of the disclosure will now be described in connection with the figures. It should be understood that for purposes of better describing the disclosure, the figures may not be to scale. Further, some of the figures include enlarged or distorted portions for the purpose of showing features that would not otherwise be apparent.

Figure 1:
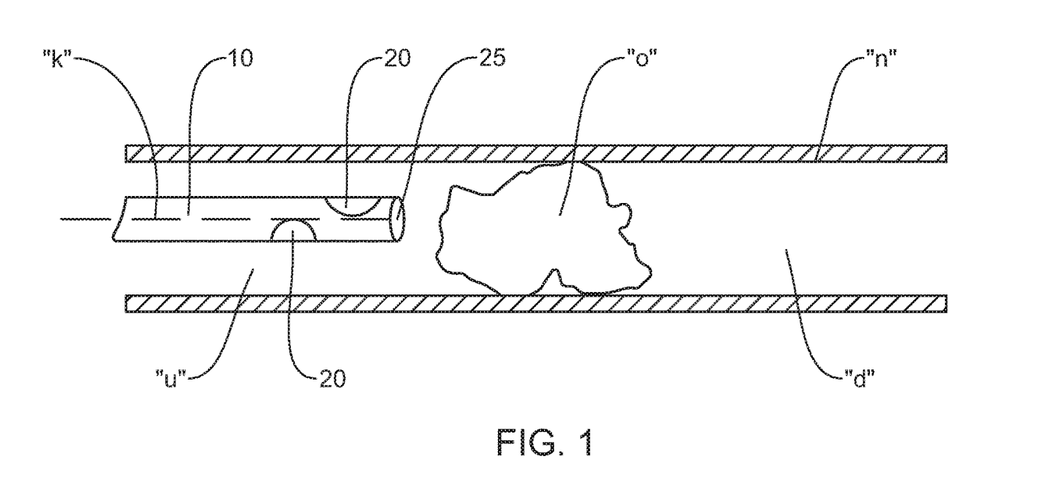
FIG. 1 is a view of a system for performing a diagnostic or therapeutic procedure incorporating an intravascular guide disposed upstream of an occlusion in a vessel.
Figure 2:
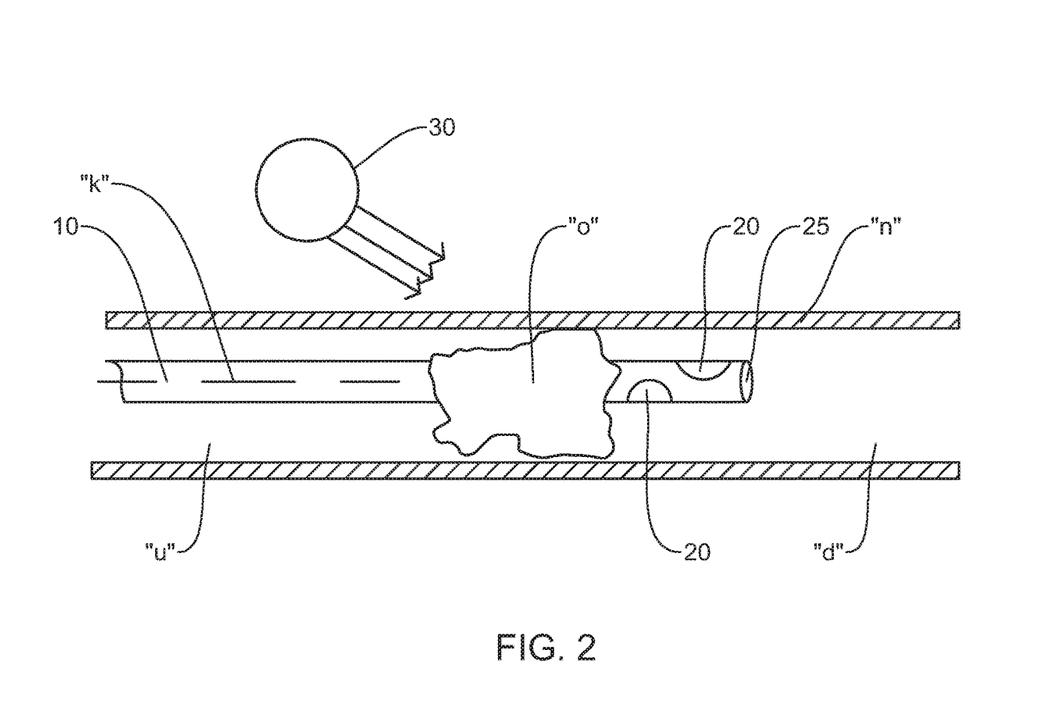
FIG. 2 is a view of the system of FIG. 1 illustrating the guide advanced through the occlusion with the sensor downstream of the occlusion.

A body or blood vessel, including a tortuous vasculature such as within the neurovascular space "n" is illustrated in the figures. In FIGS. 1-11, methods and systems are illustrated and include a guide 10 positioned at least partially within the neurovascular space "n." The guide 10 includes at least one or more sensors 20. The sensors 20 may include a pressure sensor, a flow sensor, a volume sensor or any type of sensor adapted to detect a parameter associated with the viability of vascular tissue. In some embodiments, one sensor 20 is provided. In other embodiments, multiple sensors 20 are provided (two are shown in FIGS. 1-2 as an example), and may include different sensor types, e.g., any combination of pressure, volume and flow sensors.

Examples of guidewires or catheters with pressure or flow sensing capabilities are disclosed in the literature. So-called "diagnostic wires" or "diagnostic members" are also available from Volcano (San Diego, CA) and St. Jude Medical, Inc. (St. Paul, MN). While in the illustrated embodiments, the sensor(s) 20 is/are shown positioned at a particular location on the guide 10, it is envisioned that the sensors 20 may be located at the extreme distal end or tip of the guide 10 or disposed on a location proximal of the distal tip. A volume sensor may be an infrared or ultrasonic sensor for measuring the interior volume of a segment of the blood vessel and/or the volume of blood within the segment. The pressure, flow and/or volume sensor 20 may be mounted to the guide 10 to face in a general distal direction orthogonal to the axis "k" of the guide 10 or mounted in parallel relation to the axis to face the vessel wall during application. Other angular orientations are also envisioned.

The guide 10 may be constructed to permit operation in conjunction with other devices, such as thrombectomy devices, stents, or coils while still obtaining pressure and/or flow measurements, and/or be a component of a system incorporating such devices. Alternatively, the measurement may be taken, then the guide 10 removed, the treatment delivered, and the guide 10 repositioned to take another measurement. The guide 10 may include a lumen 25 therethrough such as a microcatheter providing the ability to utilize the lumen for introduction of therapeutic elements such as embolics, drugs, micro-coils or the like.

Figure 3:
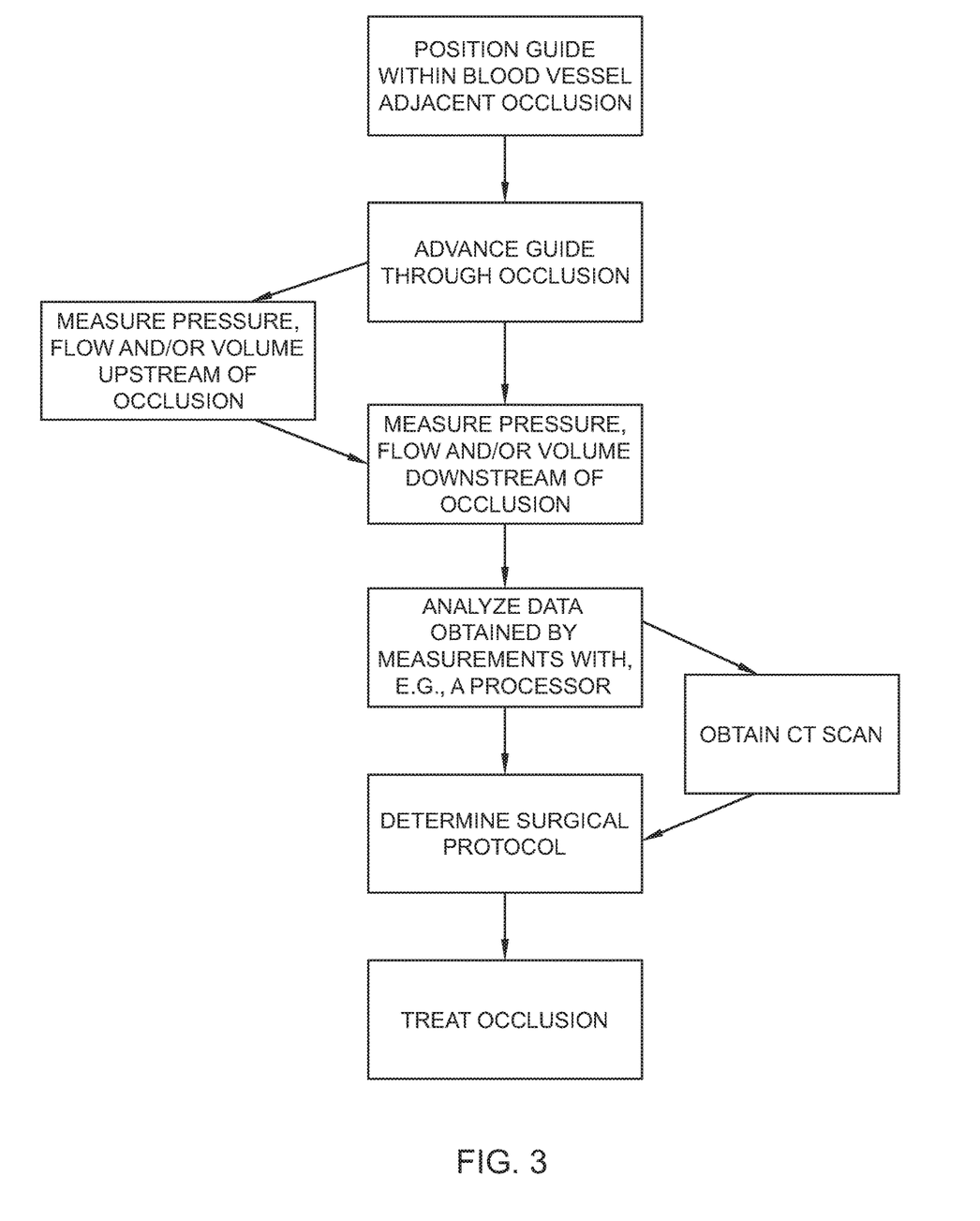
FIG. 3 is a flow chart illustrating a method of determining the viability of tissue downstream of the occlusion with the system of FIGS. 1-2.

With reference to FIGS. 1-3, a method using the system 1 to test the viability of tissue downstream of an occlusion (e.g., a partial or full occlusion) is illustrated. In FIG. 1, the guide 10 is shown proximally or upstream of the partial or total occlusion "O", and in FIG. 2, the guide 10 is shown extending through the occlusion "O". As depicted in the flow chart of FIG. 3, in conjunction with FIGS. 1-2, in embodiments, the method 100 includes positioning the guide 10 and the sensor 20 within a blood vessel adjacent an occlusion "O" (Step 102), advancing the guide 10 through the occlusion "O" such that the sensor 20 is downstream of the occlusion "O" (Step 104), measuring at least one of pressure, flow or volume downstream of the occlusion "O" using the sensor 20 of the guide 10 (Step 106), analyzing the measurements obtained from the sensor 20 (Step 108), and determining the appropriate surgical protocol based on the analyzed data (Step 110). Analyzing the measurements (Step 108) may include the use of a processor, software or logic to receive the data and provide appropriate calculations and/or output. The protocol selected may include, e.g., a thrombectomy treatment, aspiration, application of a stent, retrieval of a previously positioned stent or potentially no treatment if the determination is that the neurological tissue beyond the obstruction cannot be revitalized. In embodiments, the same guide 10 is utilized to gain access to a desired location within the body vessel "n", penetrate the occlusion "O," and to obtain the measurements associated with pressure, flow or volume within the artery or blood vessel "n".

It is envisioned that measuring the pressure, volume and/or flow (e.g., blood flow rate) downstream of at least a partial occlusion "O" provides a reliable indicator of tissue viability adjacent this location. For example, the detected pressure, volume and/or flow values obtained by the guide 10 may be compared with predetermined values based on historical or known data. Such predetermined measurements may be based on historical or empirical data developed or obtained from the patient or developed statistically from a statistical population of similar subjects. It is envisioned that if the measured values are below or above an acceptable range that viability of the tissue beyond the occlusion "O" may be ascertained to determine whether a surgical procedure is warranted or would be successful. For example, it has been determined that measuring pressure distal to an occlusion "O" (so-called "back pressure") can assist in successfully determining the viability of the tissue located distally of the occlusion "O" following thrombosis. (See, e.g., the publication entitled "Blood pressure in the artery distal to an intra-arterial embolus during thrombolytic therapy for occlusion of a major artery: a predictor of cerebral infarction following good intra-arterial" by Sorimachi, et al., in the Journal of Neurosurgery 102:870-878 (2005)).

Alternatively or additionally, the sensor 20 of the guide 10 may be utilized to measure at least one of pressure, volume and/or flow upstream of the occlusion "O" (Step 112), and this measurement(s) or data compared to the measurement (s) taken downstream of the occlusion (Step 108).

In embodiments, the same guide 10 is advanced to the occlusion "O," and pressure, volume and/or flow measurements are obtained while advancing the guide through the occlusion "O". In some embodiments, it is envisioned that measuring the pressure, volume and/or flow of at least a partial occlusion "O" may provide a reliable indicator of the length of an occluding clot. The information gained by measuring the length of the occluding clot may be used to appropriately size and/or determine the type of device used for thrombectomy.

In embodiments, the system and method described in connection with FIGS. 1-3, may further include the use of a conventional unenhanced computed tomography (CT) scan with or without the guide 10 positioned adjacent the occlusion "O" (Step 114). Specifically, the CT scan shown schematically in FIG. 2 as reference numeral 30 may be performed prior to, during and/or after the procedure to assist in assessing the condition of the downstream tissue. It is envisioned that the disclosed system and method in combination with a conventional CT scan may be used in lieu of magnetic resonance imaging (MRI) perfusion or CT perfusion techniques, which are quite expensive and time consuming, thereby saving time and money that may otherwise be spent on intervention and/or diagnostic procedures.

The system and method may include treating the occlusion (Step 116) through, e.g., the use of a thrombectomy device, such as the SOLITAIRE™ Revascularization Device, sold by Covidien (Irvine, CA). Further details of the SOLITAIRE™ device are described in U.S. Pat. No. 8,088, 140. Embodiments of the system and method also include the removal of at least a portion of the occlusion "O" using the thrombectomy device, aspiration means or the like, and measuring at least one of pressure and flow downstream of the occlusion using the sensor 20 subsequent to the removal of the occlusion "O" with the thrombectomy device. The delta or change in measured flow and/or pressure before and after application of the thrombectomy device, in conjunction with a conventional CT scan taken of the tissue may be a reliable indicator that the procedure was successful or not. Moreover, the disclosed method may be performed prior to, during, or after use of the thrombectomy device, and that measurements may be taken at anytime during the procedure with the sensor 20.

It is further envisioned that the systems and/or methods disclosed herein, can be used during diagnosis and/or treatment of ischemic strokes, and or assessing tissue damage beyond the clot in an ischemic stroke. As discussed hereinabove, measuring pressure distal to an occlusion or clot can assist in successfully determining the viability of the tissue located distally of the occlusion following thrombosis, and in conjunction with a conventional CT scan taken of the tissue may be determinative as to whether the clot should be removed.

As a further embodiment, measuring pressure, volume and/or flow upstream and/or downstream of the clot may provide an indicator of clot morphology and assist in determining the preferred thrombectomy technique such as aspiration for a soft clot or the use of a retriever device such as the aforementioned SOLITAIRE™ Revascularization Device. In other embodiments, pressure, volume and/or flow may be monitored in conjunction with drug therapy (e.g., antiplatelet therapy) to determine the effectiveness of the therapy and/or when to discontinue the drug therapy when a target flow or pressure parameter is obtained.

In additional embodiments, the guide 10 may be used with patients having atherosclerotic stenosis to measure fractional flow reserve downstream of the stenotic area within the neurovasculature. Fractional flow reserve is defined as the pressure or flow downstream of a stenosis relative to the pressure or flow upstream of the stenosis. The fractional flow reserve may be quantified as a value reflective of the percentage drop in blood pressure caused by the stenotic area. Measuring fractional flow reserve in the brain through obtaining flow and/or pressure measurements upstream and downstream of the stenotic area may provide a good indication as to which stenotic areas require stenting.

Figure 4:
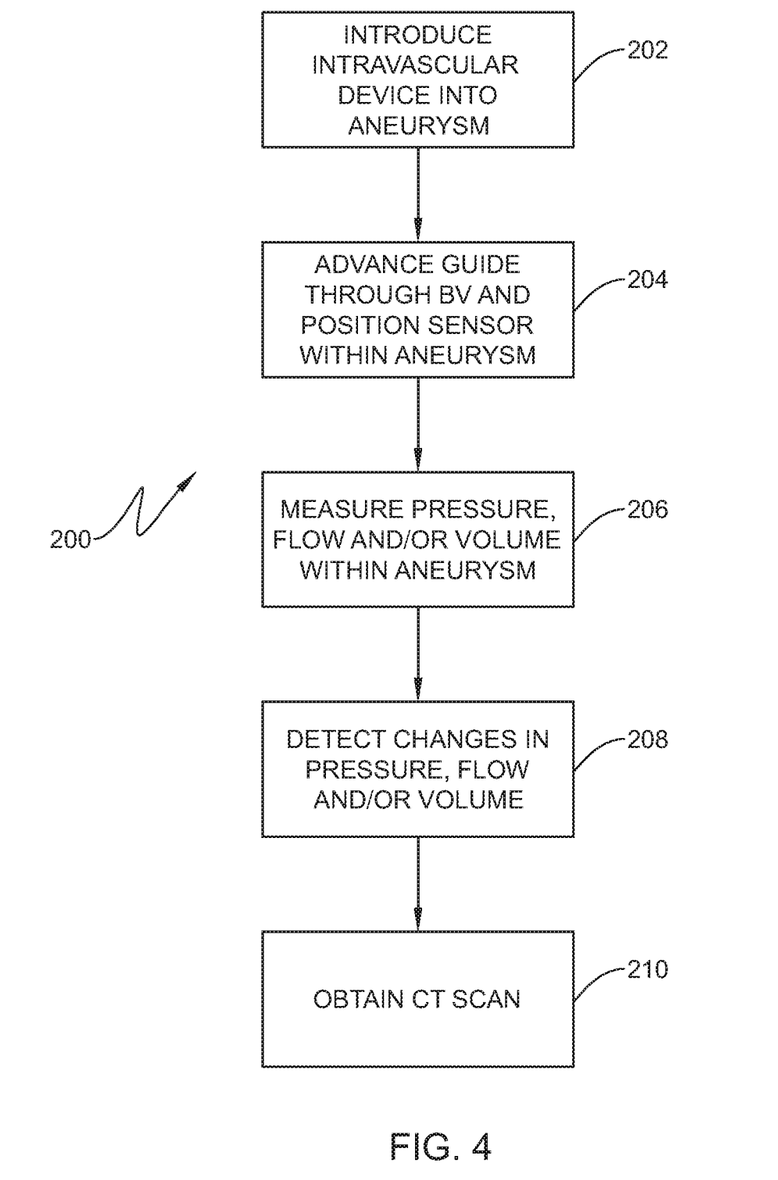
FIG. 4 is a flow chart illustrating a method for performing a diagnostic or therapeutic procedure on an aneurysm with the system of FIGS. 1-2.
Figure 5:
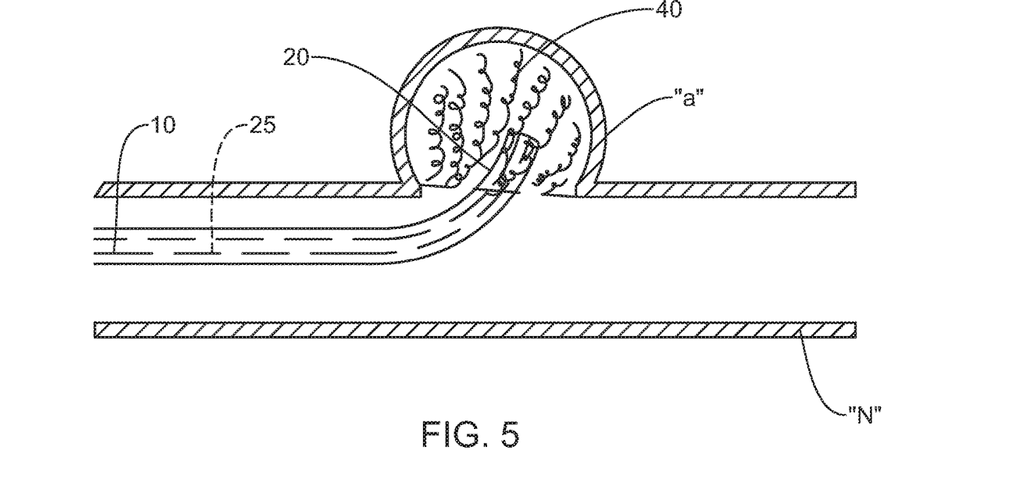
FIG. 5 is a view of the system of FIGS. 1-2 performing a diagnostic or therapeutic procedure on an aneurysm in accordance with the method embodied in the flow chart of FIG. 4.

Referring now to the flow chart of FIG. 4, in conjunction with FIG. 5, a system and method 200 for treatment of an aneurysm or an arteriole-venous malformation (AVM) is illustrated. In one system and method 200, an intravascular device is introduced through a parent vessel "n" and adjacent an aneurysm "a" to reduce blood flow from the parent vessel "n" into the aneurysm (Step 202). The intravascular device may include a plurality of coils 40 which are introduced within the aneurysm "a" to at least partially pack or fill the aneurysm "a" in connection with a neurovascular coiling procedure, or may include placement of other intravascular devices such as an expandable cage adjacent the aneurysm "a" or use of liquid embolics. The guide 10 may be utilized to introduce the coils 40 through the lumen 25 if the guide 10. The objective of the coiling procedure is to fill the aneurysm "a" or AVM with the intra-aneurysm device, e.g., coils 40, to create a clotting or thrombotic reaction to substantially close the aneurysm and prevent flow from the parent vessel "n".

The guide 10 is positioned relative to the parent vessel "n" and the sensor(s) 20 is disposed within or adjacent the aneurysm "a" (Step 204). FIG. 5 depicts the sensor 20 within the aneurysm "a". The sensor 20 is used to obtain quantifiable data including blood pressure, blood volume and/or flow velocity measurements inside or adjacent the aneurysm "a". The collected data assists in determining whether the aneurysm "a" is sufficiently packed or closed. For example, pressure, volume and/or flow velocity measurements may be taken with the sensor 20 prior to, and/or subsequent to, coil placement (Step 206). The measurements may be compared. It is theorized that the pressure, volume or flow measurements within the aneurysm "a" would be substantially less after a proper coiling procedure. Furthermore, any changes in flow, volume or pressure detected by the sensor 20 may be indicative of leakage into the aneurysm "a" from the parent vessel "n" and potentially require remedy of the aneurysm packing procedure (Step 208). A CT scan may be taken of the parent vessel "n" and the aneurysm "a" to confirm success or failure of the procedure (Step 210).

The guide 10, e.g., in the form of a microcatheter with a lumen, may be utilized to deliver the coils 40 and/or liquid embolics into the aneurysm and the pressure, volume and/or flow velocity be continually monitored until flow or pressure are stabilized indicating a sufficiently packed or occluded aneurysm sac. Suitable embolic compositions are disclosed in commonly assigned U.S. Pat. Nos. 5,667,767; 5,580,568; 5,851,508; 5,695,480; and 7,507,394.

Figure 6:
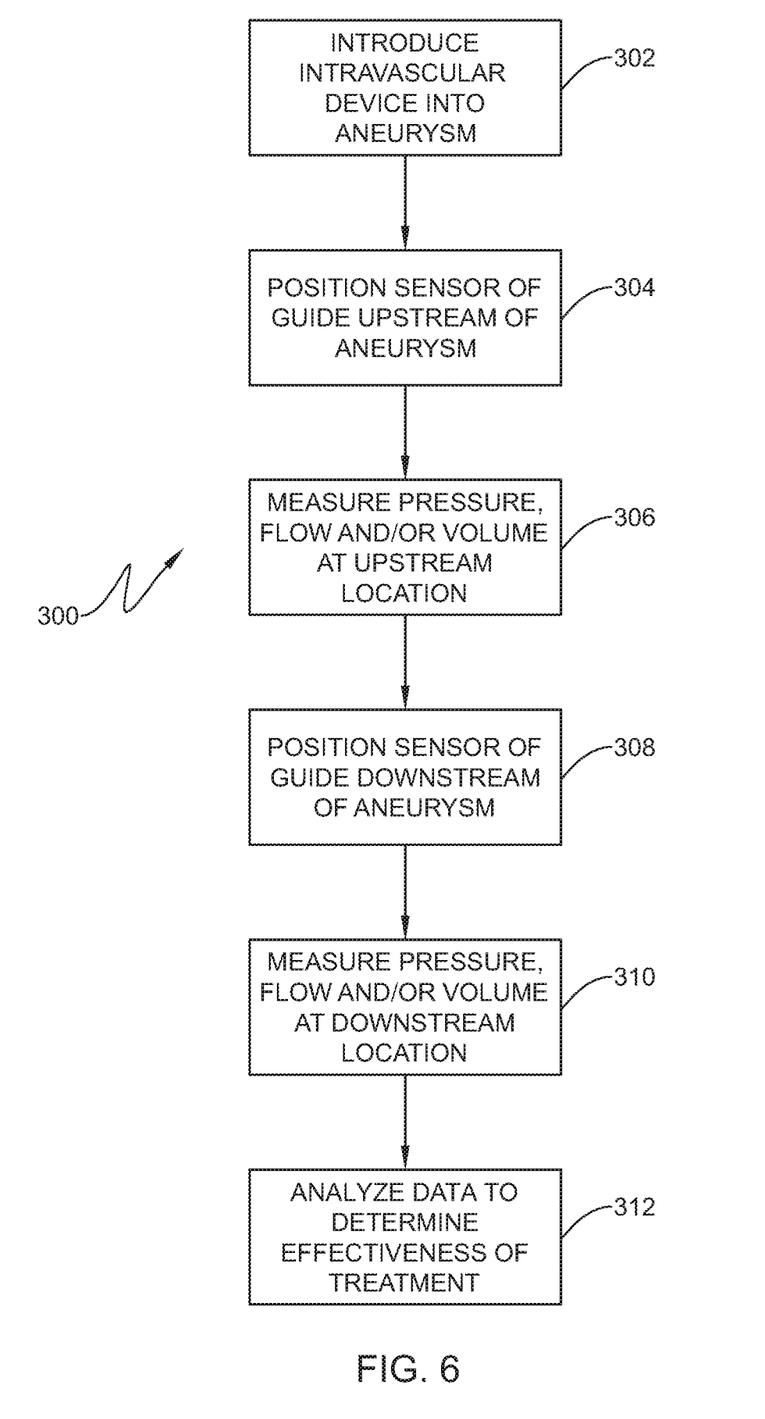
FIG. 6 is a flow chart illustrating another method for performing a diagnostic or therapeutic procedure on an aneurysm.
Figure 7:
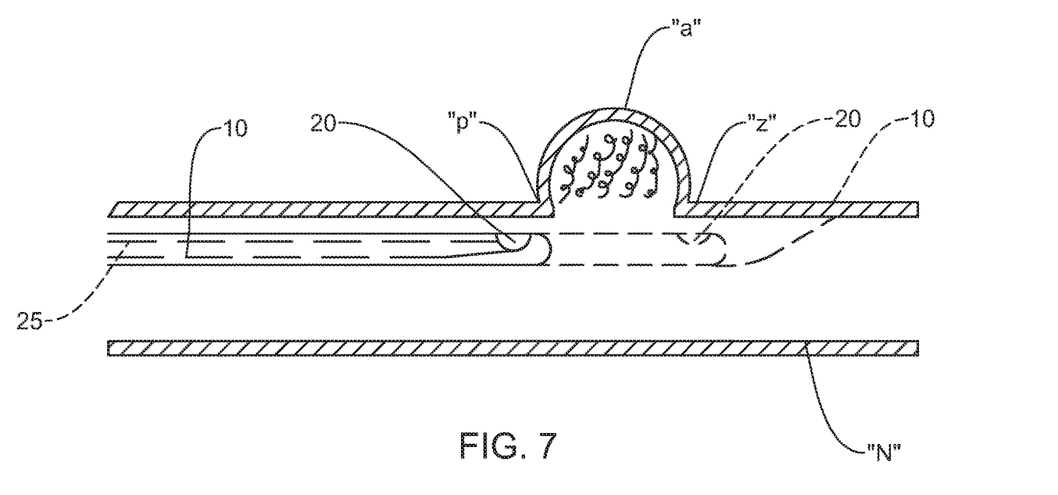
FIG. 7 is a view of the system of FIGS. 1-2 for performing a diagnostic or therapeutic procedure on an aneurysm in accordance with the method embodied in the flow chart of FIG. 6.

In another method 300 depicted in the flow chart of FIG. 6, in conjunction with FIG. 7, after the intravascular device is delivered to the aneurysm (Step 302), the sensor 20 of the guide 10 is positioned upstream of the aneurysm "a", e.g., adjacent the proximal neck "p" of the aneurysm (step 304), and pressure, volume and/or flow velocity are detected to obtain at least a first measurement (Step 306). The guide 10 is then advanced downstream of the aneurysm "a" adjacent the downstream or distal neck "z" of the aneurysm "a" (as shown in phantom in FIG. 7) (Step 308) and a second measurement of at least one of pressure, volume and/or flow downstream of the aneurysm "a" using the sensor 20 is obtained (Step 310). The first measurement and the second measurement may be compared relative to each other and/or historical data with, e.g., the use of a processor or software (Step 312). It is theorized that the pressure, volume and/or flow velocities may generally correspond at each location in the presence of a sufficiently packed aneurysm "a". In contrast, a change or difference in either pressure, volume and/or velocity at these two locations below a threshold value may be indicative of an insufficiently packed or open aneurysm, thus subjecting the patient to potential complications including rupture. It is further envisioned that a third measurement may be taken directly adjacent the aneurysm "a" between the proximal and distal necks "p", "z" and compared to the first and second measurements. As discussed hereinabove, multiple sensors 20 may be used to detect any combination of pressure, volume and velocity measurements upstream and downstream of the aneurysm "a". CT scans may be taken to confirm success or failure of the procedure.

In disclosed embodiments, the systems and methods described above relating to FIGS. 4-7 may further include calculating the difference in the measurements and comparing the difference to a predetermined value and potentially comparing these measurements against a statistical population or empirical database. When the difference is equal to or less than the predetermined value (e.g., between about 80% and about 100%), the aneurysm "a" may be deemed to be sufficiently occluded with an acceptable coil density.

In embodiments, the methods and systems of FIGS. 4-7 may be used in conjunction with conventional CT scans and/or angiography to verify that there is no leakage into the aneurysm. In an alternate embodiment, the guide 10 may be used to obtain pressure, volume and/or flow velocity measurements both prior, and subsequent to, the aneurysm "a" being packed with coils 40 at the upstream and downstream locations. The difference in these measured values may be of significance in determining the effectiveness of aneurysm closure. In disclosed embodiments, the guide 10 may be modified to both sense pressure, volume and/or flow velocity and to eject the coils 40 into the aneurysm 10. For all embodiments, the sensing function could be incorporated in a catheter or guidewire.

Figure 8:
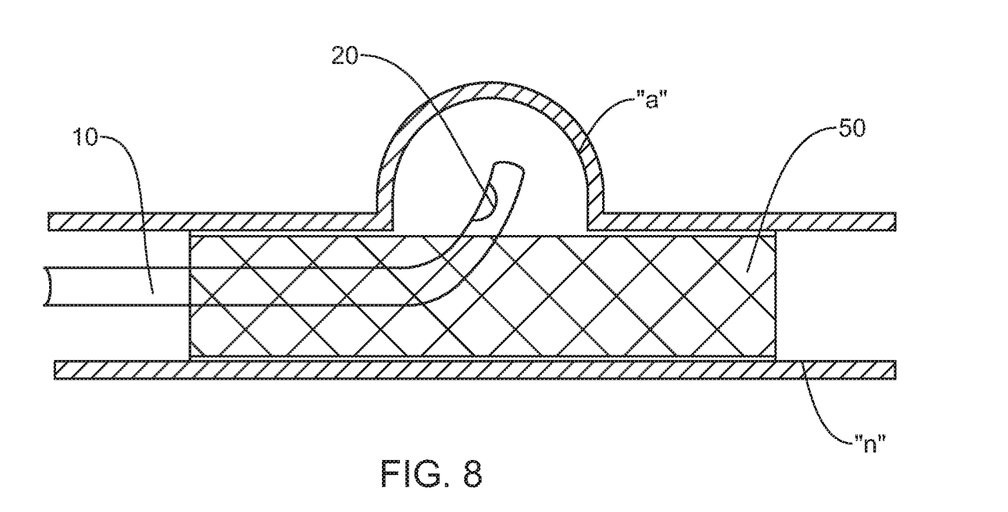
FIG. 8 is a view of the system of FIGS. 1-2 for performing a diagnostic or therapeutic procedure on an aneurysm at least partially occluded by a stent or flow diverter.

In another embodiment, and with reference to FIG. 8, the methods and systems may incorporate positioning a stent 50 through the parent vessel "n" and adjacent the aneurysm "a". The guide 10 may be manipulated through the interstices of the stent 50 to position the sensor(s) 20 within the aneurysm "a". One suitable flow diverter or stent 50 is the PIPELINE™ stent sold by Covidien LP (Irvine, CA). Further details of the PIPELINE™ stent are described in commonly assigned U.S. Pat. No. 8,267,986. The PIPELINE™ stent is self-expandable and may be placed in the parent blood vessel "n" to traverse the aneurysm "a". The braided structure of the stent 50 slows blood flow into the aneurysm "a" permitting the diseased vessel to heal. Other flow diverters or stents are also envisioned. The one or more sensor(s) 20 will obtain pressure, volume and/or flow velocity data within the aneurysm "a" to determine the effectiveness of the stent 50 in occluding the aneurysm "a". As discussed hereinabove, changes in flow, volume and/or pressure may be indicative that there is blood leakage into the aneurysm "a" requiring repositioning of the stent or the use of auxiliary intra-aneurysm devices. For example, with reference to FIG. 9, it is envisioned that the guidewire/microcatheter may be used to eject coils 40 through a lumen 25 of the guide 10 into the aneurysm "a" to supplement the functioning of the stent 50 to fill and/or occlude the aneurysm "a". In either the embodiments of FIG. 8 or 9, scanning with conventional CT modalities and/or angiography may be used to verify proper functioning of the stent.

Figure 9:
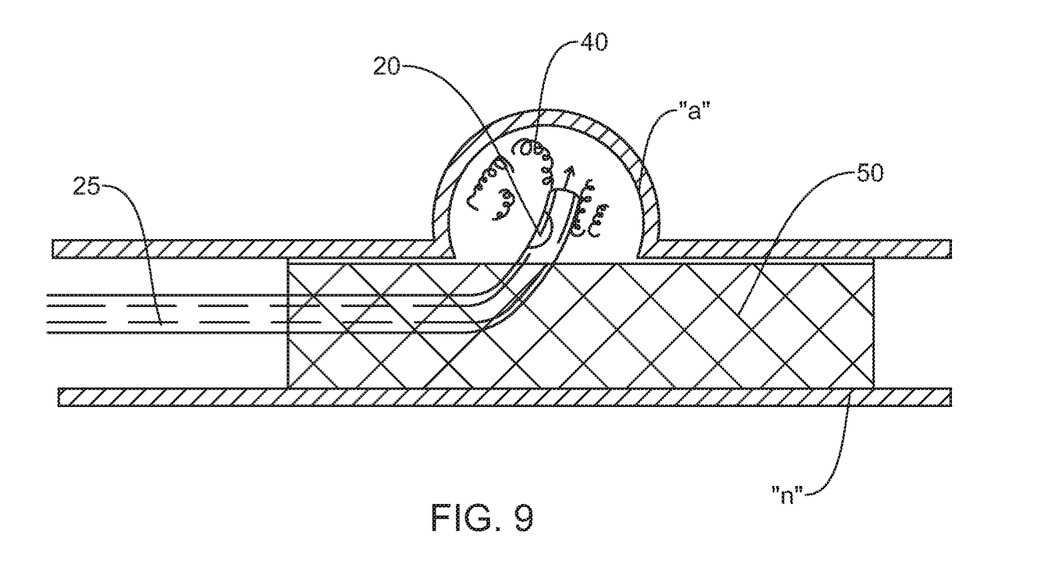
FIG. 9 is a view similar to the view of FIG. 8 illustrating use of the guide to deliver coils through the stent and into the aneurysm.

In addition, it is further envisioned that pressure, volume and/or flow measurements may be taken with the sensor 20 subsequent to deployment of the stent 50, and prior to any coiling procedure. Such measurements may provide an indication that coiling is not necessary due to effectiveness of the stent 50 in diverting blood flow. Furthermore, if the introduction of coils 40 within the aneurysm "a" is clinically needed, measurements of flow, volume and pressure may be taken at predetermined intervals during the coiling procedure to determine its effectiveness, which will potentially eliminate the unnecessary implantation of additional coils once stagnation is determined. Specifically, pressure, volume and/or velocity measurements are taken with the one or more sensors 20 to determine when to stop adding additional coils, rather than relying on packing (visual) density or retropulsion of the catheter or guide 10. This will reduce cost and procedure time.

In another embodiment, the guide 10 is advanced at least partially along the outside of the stent 50 and within the aneurysm "a" to obtain the appropriate measurements. The stent 50 will securely retain or trap the guide 10 within the aneurysm.

Figure 10:
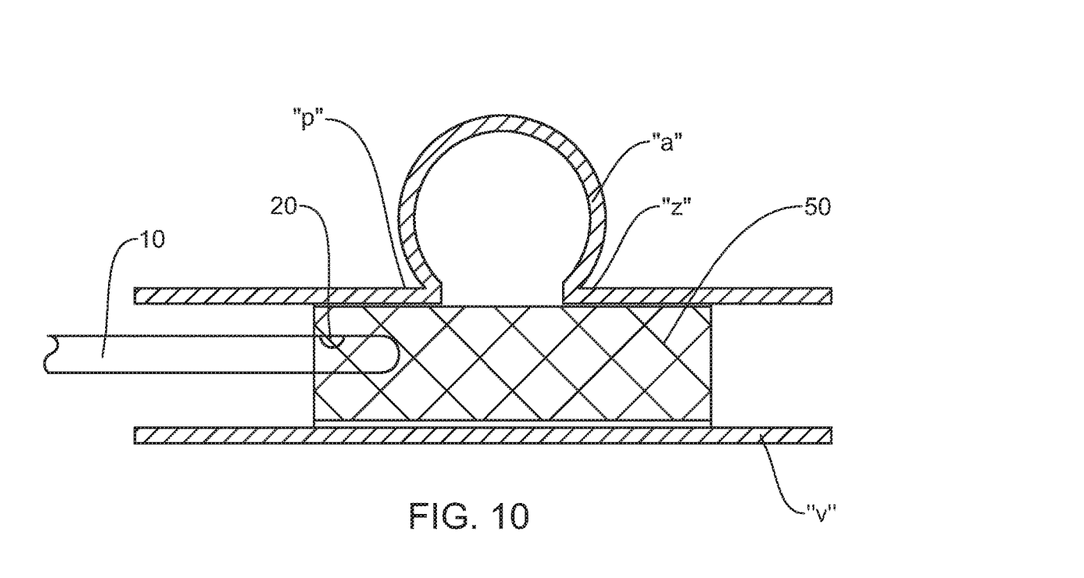
FIG. 10 is a view of a system for performing a diagnostic or therapeutic procedure incorporating the guide with the sensor disposed upstream of an aneurysm at least partially occluded by a stent.
Figure 11:
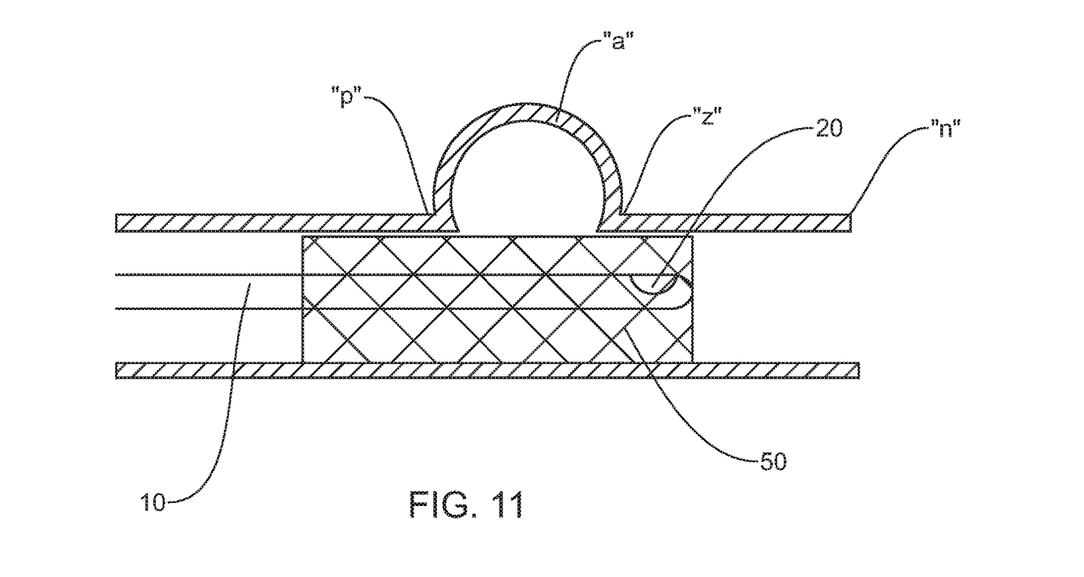
FIG. 11 is view similar to the view of FIG. 10 illustrating the guide with the sensor disposed downstream of the aneurysm.

In another embodiment depicted in FIGS. 10-11, the guide 10 is positioned such that the sensor(s) 20 is upstream relative to the aneurysm "a" and a first measurement is taken. A second measurement is taken using the sensor 20 of the guide 10 downstream relative to the aneurysm "a". Here, the same guide 10 may be used to gain access to a desired location within a vessel and to obtain the measurements. As discussed hereinabove, it is believed that the pressure, volume and or flow velocities upstream and downstream of the aneurysm "a" would generally correspond or be within comparable ranges if the stent is functioning as intended in limiting blood flow into, or closing, the aneurysm "a".

Furthermore, it is envisioned that the guide 10 may be used to measure whether placement of the stent 50 affects the elasticity of the vessel in the stent region, causing changes in the hemodynamics and potentially greater amplitude oscillations downstream of the stent 50, which may potentially lead to undesired changes in the vessel wall including tearing or rupture. Such changes of flow or pressure downstream of the stent 50 relative to upstream locations or adjacent the stent 50 may be a reliable indicator of the efficiency of stent placement relative to the aneurysm "a" and/or the potential of subsequent or current diseased conditions of the vessel wall adjacent the stent 50.

The above description and the drawings are provided for the purpose of describing embodiments of the present disclosure and are not intended to limit the scope of the disclosure in any way. It will be apparent to those skilled in the art that various modifications and variations can be made without departing from the spirit or scope of the disclosure. For example, any of the steps disclosed in the diagnostic or treatment procedures of the flow charts may occur in any sequence or order. Calculating and/or analyzing the data may include a processor, software or logic. The output data may be coordinated with software of the CT scan to provide visual, graphical or textual information to the clinician to assist in determining the treatment approach or treatment effectiveness. Thus, it is intended that the present disclosure cover the modifications and variations of this disclosure provided they come within the scope of the appended claims and their equivalents.

What is claimed is:

1. A method comprising:
    positioning a guide having a sensor configured and adapted to measure at least one of pressure, volume or flow within a blood vessel;
    advancing the guide through an occlusive clot within the blood vessel such that the sensor is downstream of the occlusive clot, and while advancing the guide through the occlusive clot, measuring at least one of pressure, volume or flow to determine a length of the occlusive clot;
    determining, based on the determined length of the occlusive clot, a size or type of a thrombectomy device; and
    introducing the thrombectomy device of the determined size or type to remove the occlusive clot.

2. The method according to claim 1 including:
    measuring the at least one of pressure, volume or flow downstream of the occlusive clot using the sensor; and
    analyzing data obtained from the sensor to assist in determining the viability of tissue of the blood vessel downstream of the occlusive clot, the data including the at least one of pressure, volume or flow downstream.

3. The method according to claim 2 including determining a surgical protocol based on analyzing the data.

4. The method according to claim 3 including obtaining a CT scan of the blood vessel and/or the occlusive clot and wherein determining the surgical protocol includes reviewing the CT scan.

5. The method according to claim 2 including treating the occlusive clot.

6. The method of claim 5 wherein treating the occlusive clot includes initiating drug therapy.

7. The method of claim 5 wherein treating the occlusive clot includes implanting a flow diverter adjacent the occlusive clot.

8. The method of claim 5 wherein measuring at least one of pressure, volume or flow downstream of the occlusive clot using the sensor is also performed subsequent to treating the occlusive clot to test effectiveness thereof.

9. The method according to claim 2 including measuring at least one of pressure, volume or flow upstream of the occlusive clot using the sensor, wherein analyzing data includes comparing measurements obtained by the sensor upstream and downstream of the occlusive clot.

10. The method according to claim 1 wherein advancing the guide through the occlusive clot vessel comprises penetrating through the occlusive clot such that the sensor is downstream of the occlusive clot.

* * * * *